United States Patent
Aykol

(10) Patent No.: US 10,847,254 B2
(45) Date of Patent: Nov. 24, 2020

(54) ARTIFICIAL INTELLIGENCE BASED STABLE MATERIALS DISCOVERY PROCESS

(71) Applicant: Toyota Research Institute, Inc., Los Altos, CA (US)

(72) Inventor: Muratahan Aykol, Santa Clara, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 419 days.

(21) Appl. No.: 15/832,278

(22) Filed: Dec. 5, 2017

(65) Prior Publication Data
US 2019/0171793 A1 Jun. 6, 2019

(51) Int. Cl.
*G16C 20/90* (2019.01)
*G16C 60/00* (2019.01)
(Continued)

(52) U.S. Cl.
CPC .......... *G16C 20/90* (2019.02); *G16C 20/10* (2019.02); *G16C 60/00* (2019.02); *G06N 20/00* (2019.01); *G16C 20/30* (2019.02); *G16C 20/70* (2019.02)

(58) Field of Classification Search
CPC ........ G06N 20/00; G16C 20/10; G16C 20/30; G16C 20/70; G16C 20/90; G16C 60/00
See application file for complete search history.

(56) References Cited

U.S. PATENT DOCUMENTS 5,434,796 A * 7/1995 Weininger ........... B01J 19/0046
703/12
7,447,614 B2 * 11/2008 Ghaboussi .............. G06F 30/20
703/2
(Continued)

FOREIGN PATENT DOCUMENTS

CN 106447229 A 2/2017

OTHER PUBLICATIONS

Ward et al.; "Including crystal structure attributes in machine learning models of formation energies via Voronoi tessellations"; Phys. Rev. B; 2017 (Year: 2017).*
(Continued)

*Primary Examiner* — Roy Y Yi
*Assistant Examiner* — Geoffrey T Evans
(74) *Attorney, Agent, or Firm* — Christopher G. Darrow; Darrow Mustafa PC

(57) ABSTRACT

An existing materials database (EMDB) is a compilation of inorganic materials with composition and crystal structures known from prior experimental synthesis and characterization reports, or from ab initio or other computational studies, and includes a composition, structure, and stability value for each material. A hypothetical materials database (HMDB) is an extremely large compilation of materials of unknown stability and synthesizability, with no explicitly available or accessible prior experimental or computational report of their structure-composition combinations. An automated process for efficiently expanding the size of an EMDB includes a cyclical sub-process in which a rapid algorithm provides preliminary stability estimates for hypothetical materials selected from an HMDB, and those materials with a favorable stability prediction undergo a full ab initio analysis to obtain quantitative stability values and are then added to the EMDB. During each iteration of the cyclical
(Continued)

sub-process, the rapid algorithm is trained on the EMDB, so that it becomes more effective at providing preliminary stability estimates with each iteration, as the EMDB expands.

20 Claims, 3 Drawing Sheets

(51) Int. Cl.
     *G16C 20/70*     (2019.01)
     *G06N 20/00*     (2019.01)
     *G16C 20/30*     (2019.01)
     *G16C 20/10*     (2019.01)

(56) References Cited

U.S. PATENT DOCUMENTS

| | | | |
|---|---|---|---|
| 7,996,156 B2 * | 8/2011 | Beger | G01N 33/48 702/19 |
| 8,843,509 B2 | 9/2014 | Csanyi et al. | |
| 8,862,520 B2 * | 10/2014 | Agarwal | G06N 20/00 706/12 |
| 10,515,715 B1 * | 12/2019 | Pappas | G06N 20/00 |
| 2006/0074594 A1 | 4/2006 | Ceder et al. | |
| 2014/0236548 A1 * | 8/2014 | Conduit | G16C 20/30 703/2 |
| 2015/0310162 A1 * | 10/2015 | Okuno | G16C 20/50 706/12 |
| 2017/0217796 A1 | 1/2017 | Snydacker et al. | |
| 2017/0229742 A1 | 8/2017 | Aykol | |
| 2018/0253454 A1 * | 9/2018 | Botea | G06F 16/2455 |

OTHER PUBLICATIONS

Hautier et al.; "Finding Nature's Missing Ternary Oxide Compounds Using Machine Learning and Density Functional Theory"; Chem . Mater. (Year: 2010).*

Jain, A. et al., "Commentary: The Materials Project: A materials genome approach to accelerating materials innovation," APL Materials, 1, 011002 (2013).

Kirklin, S. et al., "The Open Quantum Materials Database (OQMD): Assessing the Accuracy of DFT Formation Energies", npj Computational Materials, 1, 15010 (2015).

Cohn, D.A. et al., "Active learning with statistical models," Journal of Artificial Intelligence Research, 4, pp. 129-145 (1996).

Settles, B., "Active Learning—Synthesis Lectures on Artificial Intelligence and Machine Learning", Morgan & Claypool Publishers, ISBN: 9781608457250 (2012).

Wang, L. et al., "Active learning via query synthesis and nearest neighbour search", Neurocomputing, 147, pp. 426-434 (2015).

Balachandran, P. et al., "Adaptive Strategies for Materials Design using Uncertainties", Scientific Reports, 6, 19660 (2016).

Saal, J.E. et al., "Materials Design and Discovery with High-Throughput Density Functional Theory: The Open Quantum Materials Database (OQMD)", JOM, vol. 65, No. 11, pp. 1501-1509 (2013).

Meredig, B. et al, "Combinatorial screening for new materials in unconstrained composition space with machine learning," Physical Review B 89, 094104 (2014).

Jain, A. et al., "Performance of genetic algorithms in search for water splitting perovskites", J Mater Sci 48:6519-6534 (2013).

Ward, L. et al., "Atomistic calculations and materials informatics: A review," Current Opinion in Solid State Materials Science, 21, pp. 167-176 (2017).

* cited by examiner

ARTIFICIAL INTELLIGENCE BASED STABLE MATERIALS DISCOVERY PROCESS

TECHNICAL FIELD

The present disclosure generally relates to digital computing methods adapted to chemoinformatics and materials informatics and, more particularly, to automated systems and methods for expanding a materials database and identifying materials having a desired property.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Inorganic materials having specialized properties are essential to a large proportion of industrial efforts, including such as energy generation and storage, thermal insulation and conduction, chemical catalysis, and many others. Efforts to identify and develop materials having desired properties benefit from the existence of large databases of known materials with tabulated properties; ideally for materials that have been made or are stable enough to be synthesized.

Ab initio methods like Density Functional Theory calculations (DFT), including high throughput DFT, have been used to expand databases of known materials by providing quantitative stability values, and thus determinations of synthesizability, of hypothetical materials derived by populating prototype crystal structures with a variety of elements. However, due to the relatively high computational resource requirements of DFT, these approaches are limited in the rate of database growth, and often require significant human intervention and/or direction.

Accordingly, it would be desirable to provide an improved method to rapidly and automatically expand databases of known materials at the minimal computational cost.

SUMMARY

This section provides a general summary of the disclosure, and is not a comprehensive disclosure of its full scope or all of its features.

In various aspects, the present teachings provide an automated process for expanding an existing materials database (EMDB). The process includes providing a hypothetical materials database (HMDB), the HMDB including a compilation of hypothetical materials. For each material, the HMDB includes a unique combination of a composition and a crystal structure including a set of atomic coordinates, and dimensions and shape of the unit cell. The HMDB can be generated by decorating each of a plurality of prototype crystal structures with all possible compositions to produce a plurality of hypothetical materials. The process also includes a cyclical sub-process that is performed at least two times, and can be performed any greater number of times. The cyclical sub-process includes a step of training a predictive model (PM) to generate a preliminary stability value for a material, based on the materials composition and structure. The PM is trained, based on the contents of the EMDB, which include a compilation of known materials, properties of which are previously calculated with an ab initio quantum mechanical method, and for each material in the compilation: a composition, a crystal structure including atomic coordinates of atoms, shape and dimensions for a unit cell, and a stability value. The cyclical sub-process further includes a step of applying the PM to at least a portion of the HMDB to produce a preliminary stability value for each hypothetical material in the portion. The cyclical sub-process further includes a step of selecting a subset of the set, the subset consisting of all hypothetical materials in the set having a preliminary stability value greater than a predetermined threshold value. The cyclical sub-process also includes a step of performing ab initio calculations on the subset, to determine the quantitative stability value for each hypothetical material in the subset, thereby converting each hypothetical material in the subset to a new material. The cyclical sub-process further includes a step of adding each new material in the subset, with its composition, crystal structure, and stability value, to the EMDB to generate a larger EMDB.

Further areas of applicability and various methods of enhancing the disclosed technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein.

It should be noted that the figures set forth herein are intended to exemplify the general characteristics of the processes, algorithms, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DETAILED DESCRIPTION

The present teachings provide processes for the automated and rapid expansion of an Existing Materials Database (EMDB), in particular by augmenting the EMDB with materials determined to be stable and therefore synthesizable. The present processes also provide efficient computational identification of materials having a desired property at a threshold level.

The processes of the present teachings begin with a Hypothetical Materials Database (HMDB), having a very large number of hypothetical but unknown materials. A computationally non-intensive algorithm is used to rapidly generate a compilation of materials selected from the HMDB that are likely to be stable, for example, with respect to decomposition into other materials. This acts as a screen to quickly eliminate materials unlikely to be stable, so that more substantial computational and time resources are not wasted on them. The materials predicted likely to be stable are then assessed for quantitative stability determination, and added to the Existing Materials Database.

Figure 1:
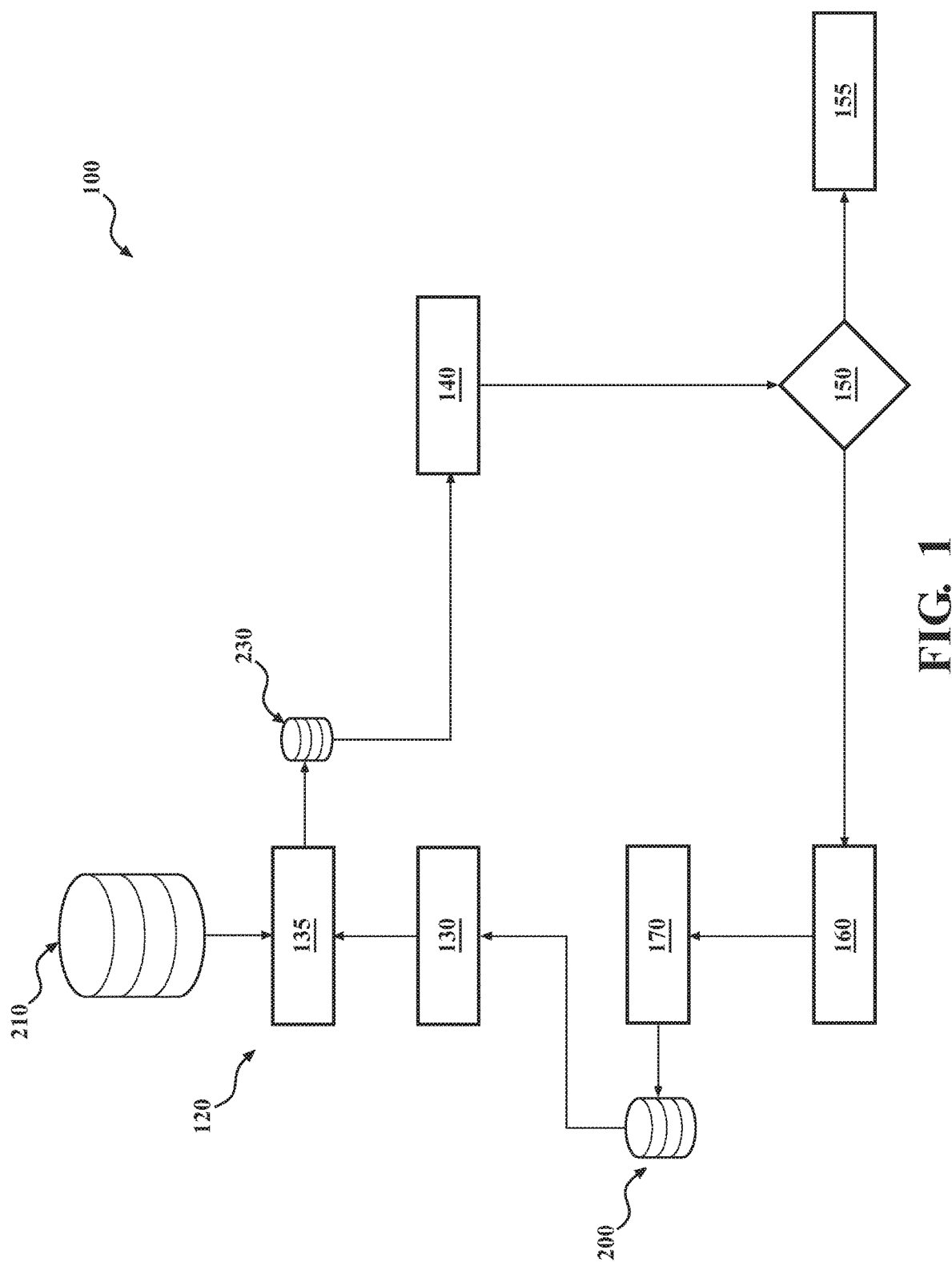
FIG. 1 is a flow chart of a process for expanding an existing materials database.
Figure 2:
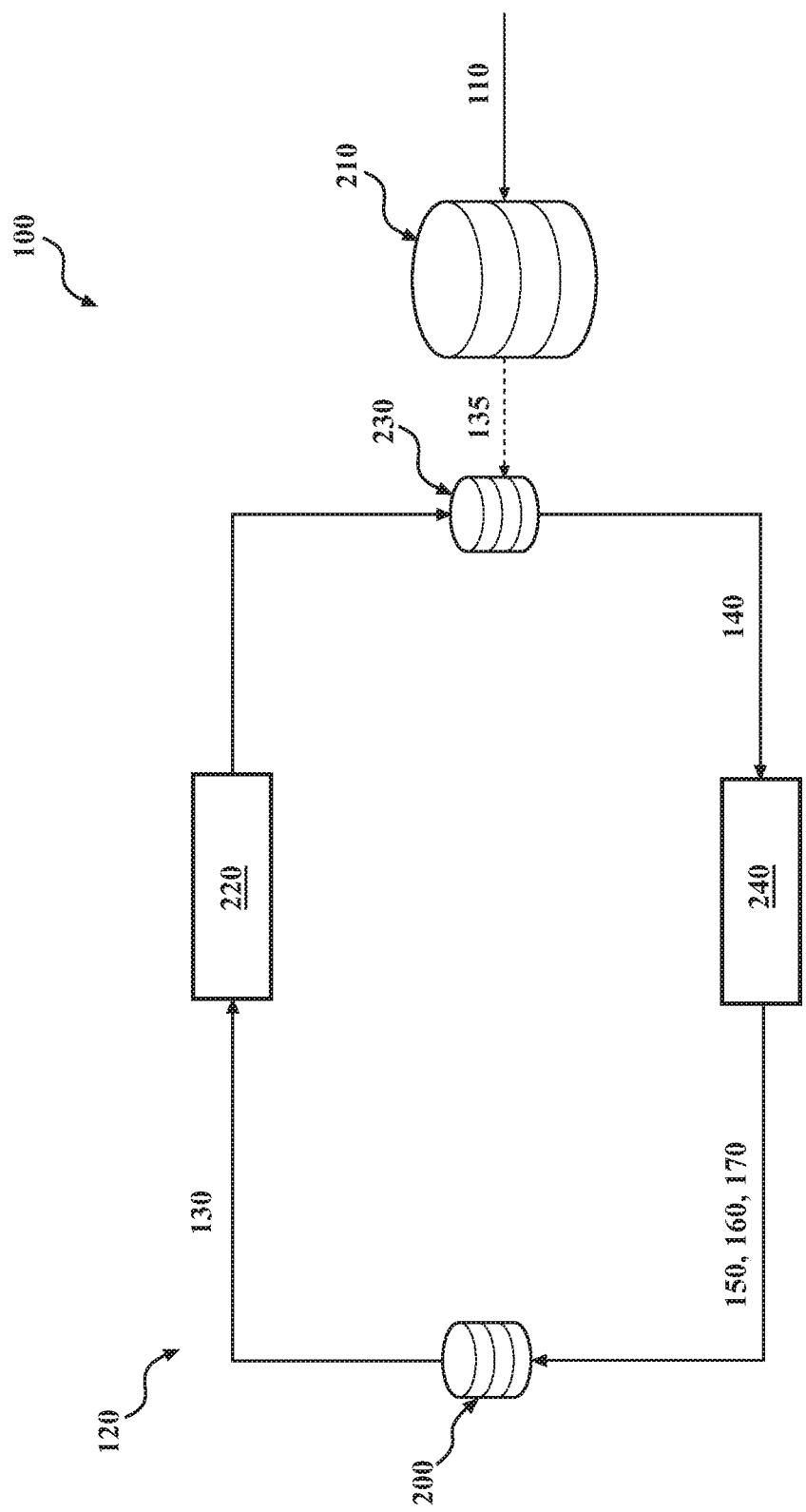
FIG. 2 is an object-based flow chart of the process of FIG. 1.

Accordingly, and with reference to FIGS. 1 and 2, a process 100 for expanding an EMDB 200 is disclosed. As used herein, the phrase "Existing Materials Database" refers to a digitized compilation of inorganic materials, each with a known structure and a known set of properties. Initially, an EMDB 200 can include materials that have been synthesized, such as those with structures available in the Inorganic Crystal Structure Database, American Mineralogist Crystal Structure Database, Crystallography Open Database, Pauling File Database and alike, as well as materials that have not been synthesized but are known from previous ab initio calculations or empirical methods. This initial set of materials in the EMDB 200 can include materials that are thermodynamically stable in the ground state or those energetically close to the ground state, and therefore likely synthesizable as well as materials that are thermodynamically unstable or far from the ground state. The cyclic sub-process that will be described below is designed to ensure that materials added to the EMDB 200 from an HMDB 210 will predominantly be thermodynamically stable or nearly stable materials, and therefore likely synthesizable.

Each entry of a material in the EMDB 200 further includes, for that material, at least: a composition; a stability value; and a crystal structure, generally including dimensions and shape of the unit cell and atomic coordinates in the unit cell. The stability value can be empirically determined or determined by ab initio calculations. As used herein, the phrase "ab initio calculations" refers to first principles quantum chemistry computational methods to solve the Schrödinger equation for molecules, and crystalline and non-crystalline materials, such as: Density Functional Theory (DFT), and various Wavefunction Theory based approaches, such as Hartree-Fock and related methods; configuration interaction methods; Møller-Plesset perturbation theory, hybrid DFT methods; van der Waals inclusive DFT methods; random phase approximation, or coupled cluster theory.

The HMDB 210 can be provided or the systems and processes 100 can include a step of generating 110 an HMDB 210. The HMDB 210 includes a compilation of inorganic materials that could exist, but not previously examined computationally with ab initio methods or made and/or characterized experimentally, and therefore not known to be stable/synthesizable and/or whose stability has not been evaluated. Such materials are referred to herein as "hypothetical materials." The HMDB 210 will include, for each hypothetical material compilation, a composition and a crystal structure, analogous to the composition and crystal structure contained for each material in the EMDB 200. The crystal structure of a hypothetical material can be alternatively referred to herein as a "hypothetical crystal structure."

The HMDB 210 can be generated, in one approach, by decorating one or more prototype crystal structures, having prototype formulae (such as $AB_3$) with all possible elements, thus automatically providing the composition and the crystal structure for each hypothetical material. For example, an $L6_0$ (Strukturbericht notation) prototype structure, having two elements at relatively well-defined coordinates, could give rise to a large number of hypothetical materials by substitution of every possible element for each of the two elements present in the $L6_0$ prototype structure. In practice, 80-90 elements may be included in each position in the prototype formula, excluding for example noble gases and/or actinides. It will thus be appreciated that the HMDB can rapidly become very large, with a virtually unlimited potential number of hypothetical materials. For example, a single binary (two element) prototype structure such as $L6_0$ can yield over $6 \times 10^3$ hypothetical materials, and a single quaternary (four element) prototype structure such as $F5_9$ can yield over $4 \times 10^7$ hypothetical materials. In addition, as a result of the process of an exhaustive decoration of prototype crystal structures with all chemical elements, a small fraction of hypothetical materials generated may already have equivalents in the initial EMDB 200, and therefore can be excluded from HMDB 210.

It will further be appreciated that the HMDB 210 can include a substantial number of hypothetical materials that are thermodynamically unstable, and thus difficult or impossible to synthesize. For instance, substitution of an electronegative element at a site that is occupied by metals in all known structures could be expected to produce hypothetical materials that would prove to be unstable. In some implementations, restrictions can be applied at the step of generating 110 the HMDB 210 as a means of applying conventional chemical knowledge to exclude such potentially unstable species. For example, in a given prototype structure, the available elements for any position could be restricted to elements having electronegativity within a specified number of Pauling units of the average electronegativity of elements occupying the site in all known materials having the same prototype structure. Alternatively or in addition, restrictions could be based on atomic radius, or any other suitable property by which elements can be categorized. In some implementations however, and in consideration of the automated nature and speed of the process 100, it will be desirable to avoid placing any assumptions or restrictions on the step of generating 110 the HMDB 210. This approach can allow a system operating the process 100 to explore the maximum compositional space, and to avoid overlooking possible stable materials that would defy such assumptions. In addition, and as discussed in greater detail below, the inclusion of unstable materials or materials that do not conform with principles derived from basic chemical knowledge in the HMDB 210 can enable the process 100 to become more efficient over time.

The process 100 further includes a cyclical sub-process 120 that can be repeated any number of times. The cyclical sub-process 120 includes a step of training 130 a Predictive Model (PM) 220 with the EMDB 200. The PM 220 is an algorithm that predicts the stability of a material, requiring minimal time and computational resources. As noted above, each compilation of a known material in the EMDB 200 includes a composition; a crystal structure; and a stability value. Thus, in the training 130 step, the PM 220 algorithm surveys the landscape of all known materials, including their structure, composition, and quantitative stability, in a machine-learning process to improve its ability to quickly predict the stability of a material with reasonable, but less than quantitatively rigorous, accuracy.

The PM 220 can be trained with the assistance of a material descriptor vector generator. For instance, for every material in the EMDB 200 and HMDB 210, a vectorized collection of descriptors for each material can be generated. A descriptor vector can consist of any information that can be used to differentiate two different materials when used as input for a machine learning algorithm of the PM 220. A descriptor vector typically can contain many descriptors, each position in the vector occupied by the same type of descriptor for every material. Descriptors can be derived from structural, chemical, or compositional variables of the material, as well as elemental properties of constituent elements. In general, correlation between unique descriptors in a descriptor vector of a material will be minimal, but this is not required.

In some implementations, descriptors can be generated by applying statistical aggregators on the array of elemental, structural and compositional properties for a given material, including but not limited to functions like minimum, maximum, range, mean, median, variance, kurtosis, and skewness. One can assume equal weights, or apply specified weights during statistical aggregation. For example, compositions of the elements making up the material or structural descriptors like coordination numbers can further be used as weights when applying statistical functions like "mean" during aggregation. The number of descriptors can further be increased by polynomialization, for example by multiplying unique descriptors to create new descriptors, and/or other mathematical combinations of descriptors based on chemical or physical knowledge, or empirical or fundamental theories. In some implementations, descriptor vectors can be extended by, or derived from, a standardized binning of partial or total atomic pair-wise correlation functions and/or radial distribution functions and the like, and their real or reciprocal space transformations, to describe a given material.

In order to prepare the descriptor vectors as input for machine learning algorithms, descriptors can be subjected to statistical procedures like standardization, normalization, scaling, transformations, and/or encoding. A subsequent process may be used to reduce the number of descriptors to be used in training of the PM 220 by employing principal component analysis, or other variance-based statistical metrics for algorithmically selecting or deriving the most informative set of features. This is not an exhaustive list of methods by means of which material descriptors can be generated. The descriptor generation process can vary among different implementations without affecting the flow of the overall process described here, because the process has no explicit dependence on the exact nature of the descriptor vectors as long as they can be generated in a reasonable computation time and provide sufficient statistical accuracy for the PM during training, testing and application.

The cyclical sub-process 120 can include a step of selecting 135 a set 230 that includes at least a portion of the HMDB 210. The phrase, "at least a portion of the HMDB 210" refers to a compilation of some, but not necessarily all, of the hypothetical materials in the HMDB 210. The set 230 will include the composition and crystal structure for each hypothetical material included in the set 230.

It will be understood that, in many implementations, the set 230 will constitute a small percentage of the HMDB 210, particularly in instances in which the HMDB 210 is very large. For example, and as alluded to above, the HMDB 210 can be as large as $10^9$ hypothetical materials, or many orders of magnitude larger, virtually without limit. In contrast, the set 230 can, in some implementations, have on the order of $10^5$-$10^6$ hypothetical materials. In some implementations, hypothetical materials can be randomly selected from the HMDB 210 to form the set 230. In some implementations, the step of selecting 135 the set 230 will include selecting a group of structurally and/or compositionally related hypothetical materials, such as hypothetical materials having the same or similar prototype structure. In some implementations of the process 100, during or after performance of the selecting 135 step, all hypothetical materials selected for inclusion in the set 230 will be removed from the HMDB 210 prior to the next iteration of the cyclical sub-process 120, so that the HMDB 210 becomes smaller with each iteration of the cyclical sub-process 120.

The cyclical sub-process 120 can further include a step of applying 140 the PM 220 to the set 230. The step of applying 140 the PM 220 to the set 230 produces a preliminary stability value for each hypothetical material contained in the set 230. The preliminary stability value produced by the PM 220 in the applying 140 step will be the same type of stability value as those contained in the EMDB 200, such as heat of formation (or formation energy) and subsequent thermodynamic stability metrics that can be analytically derived from heat of formation. The PM 220 can be configured to take material descriptor vectors as input and produce the heat of formation using any machine-learning algorithm from a variety of known options, such as linear regression methods, tree based regression methods, kernel-based methods, neural network regression methods, Bayesian regression methods, regularized-models such as those based on ridge or lasso methods, support vector machine regression, Gaussian regression, or the like, or combinations of these methods. Standard regression practices such as cross-validation should be followed.

The cyclical sub-process 120 can include a step of selecting 150 a subset 240 from the set 230 by discarding 155 hypothetical materials in the set 230 predicted to have stability that does not meet a threshold. One such stability metric would be energy distance of a material to the heat of formation convex-hull of the EMDB 200; where "convex hull" refers to a subset of materials in the EMDB 200 that provides the lowest-energy combinations of materials in the EMDB 200 at the time of application, for all compositions. This heat of formation distance can be defined as the difference between the heat of formation predicted by the PM 220 for a material not in the EMDB 200, and the heat of formation at the EMDB 200 convex-hull. Defined this way, a negative or zero distance indicates ground state thermodynamic stability, whereas a positive distance implies metastability or instability with respect to existing materials in the EMDB 200. A larger positive distance indicates a stronger tendency or thermodynamic driving force to decompose into lower energy combinations of other phases available in the EMDB 200. For example, any hypothetical material having a heat of formation distance to the EMDB 200 convex-hull greater than a pre-determined threshold value can be discarded 155 at or after the selecting 150 step, such that all hypothetical materials in the set 230 that are not discarded 155 are selected 150 for the subset 240. In some implementations, the pre-determined threshold value can be in the range between a more restrictive value like zero eV/atom and a less restrictive value like 0.1-0.2 eV/atom, or higher. In some implementations, hypothetical materials can be deleted from the HMDB 210 once they are discarded 155 from the set 230. In some implementations, a pre-determined small fraction of hypothetical materials in set 230 that would otherwise be discarded 155 can instead be selected 150 for the subset 240, to provide negative examples of stability (i.e. examples of instability for PM 220 training purposes) and subsequently increase the predictive accuracy of the PM 220 in the next iteration.

The cyclical sub-process 120 includes a step of performing 160 ab initio calculations on each hypothetical material in the subset 240, to produce a quantitative stability for each hypothetical material in the subset 240. An ab initio calculation can involve relaxation of all structural degrees of freedom of the hypothetical material to its ground state geometric configuration to obtain its ground state internal energy, and thus the heat of formation by referencing this energy to standard thermodynamic reference states of constituent elements. Typically, empirical corrections determined a priori and independent of this process (for example, by calibrating the reference energies by fitting to experimental heats of formation) can be applied to this heat of formation to improve its chemical accuracy. Pressure-volume contributions may be included, but typically they are negligible when evaluating heat of formation at low/close-to-ambient pressures for inorganic solids. In addition, the initial structure of a hypothetical material derived from a prototype may be far from its geometric ground state. Therefore, in order to save computational resources at the ab initio relaxation step, the initial structure parameters (such as any or all of the parameters of the crystal structure as described above, or a unit cell volume) of a hypothetical material in 240 can be rescaled to reproduce a predicted ground state volume. This can be achieved by training a reasonable predictive modeling algorithm for volume per atom of a material using the available volume information of existing materials in the EMDB 200. The modeling algorithm can be created with a process analogous to the regression methodologies described above with respect to the PM 220, but in contrast, this predictive modeling algorithm is auxiliary in nature, with a purpose to accelerate convergence of ab initio calculations by providing a reasonable initial guess for the absolute value of structure parameters prior to relaxation. It is not an essential component of the cyclic process and can be excluded; can be trained only once during the first iteration of the cyclical sub-process 120; or can be trained multiple times—once per iteration over multiple iterations of the cyclical sub-process 120. Therefore, after the ab initio calculation, each hypothetical material in the subset 240 will have associated with it: (i) a composition; (ii) a crystal structure; and (iii) a quantitative stability. The performing 160 ab initio calculations step thus converts each hypothetical material in the subset 240 into a new material. Suitable ab initio calculations can include any calculations discussed above in connection with the EMDB 200.

Figure 3:
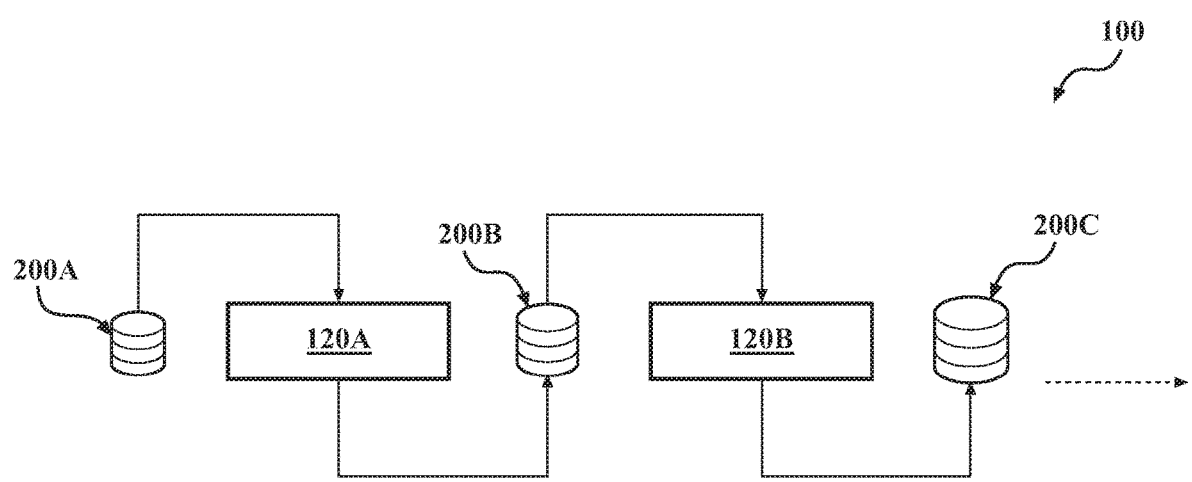
FIG. 3 is a flow chart illustrating expansion of an existing materials database as a result of multiple iterations of the process of FIGS. 1 and 2.

The cyclical sub-process 120 thus includes a final step of adding 170 each new material in the subset 240, created by performing 160 ab initio calculations, to the EMDB 200. This has the effect of producing an EMDB 200 at the end of each cycle that is larger than the EMDB 200 of the previous cycle. For example, and with reference to FIG. 3, the initial EMDB 200A, prior to performance of a first iteration of the cyclical sub-process 120, has a size defined by the number of existing materials, X, that it contains. After a first iteration of the cyclical sub-process 120A, a larger EMDB 200B is created, having a size defined by the number of currently existing materials, X', that is equal to the sum of X and the subset 240 that was selected and added to the EMDB 200A during the first iteration of the cyclical sub-process 120A. Similarly, a second iteration of the cyclical sub-process 120B produces a larger still EMDB 200C, having a size defined by the number of currently existing materials, X", that is equal to the sum of X' and the subset 240 that was selected and added to the EMDB 200B during the second iteration of the cyclical sub-process 120B, and so forth.

In general, the cyclical sub-process 120 will be repeated at least once (two iterations). In some implementations, the cyclical sub-process will be repeated at least twice (three iterations). In some performances of the process 100, the cyclical sub-process will undergo at least three or more iterations, such as 10, or $10^2$, or $10^3$, or $10^4$, or $10^5$ or more iterations. There is no restrictive upper limit on the number of iterations, and iterations can optionally continue until the hypothetical materials available in the HMDB 210 are exhausted or until the PM 220 reaches a predictive accuracy identical to the ab initio method as measured with respect to the ground-truth in EMDB, obviating the further need to perform ab initio calculations.

It will be apparent that the present process 100 accelerates the rate of productive EMDB 200 growth, in which computational resources are focused on finding synthesizable materials (materials with higher likelihood of synthesis with experimental techniques), by enabling the PM 220, via the selecting 150 step, to quickly remove unsynthesizable materials so that resources are not wasted on them.

Because every iteration or repetition of the cyclical sub-process 120 increases the compositional and structural landscape covered by the EMDB 200, each iteration improves the quality of the training 130 of the PM 220. That is, the training 130 in each subsequent iteration will be formed on the basis of the contents of the larger EMDB 200B, 200C, etc., giving the PM 220 a more expansive training landscape and thus improving the accuracy and efficiency of the PM 220. In addition, the PM 220 will be afforded the opportunity to learn from its false positives. Each time that the PM 220 predicts a hypothetical material to be stable, but ab initio calculations determine the material is unstable, that material will still be added to the EMDB 200, and thus during the next training 130, the PM 220 will learn from its mistake. In addition, as described above, a small number of unstable materials can be selected 150 for ab initio calculations and eventual inclusion in the EMDB 200, to accentuate PM 220 training via the inclusion of negative examples.

It will be appreciated that the process 100 could be used to enrich an EMDB 200 with materials having a specific property in addition to stability/synthesizability. For example, the performing 160 ab initio calculations could be modified by employing DFT or other ab initio calculations designed to predict band gap, magnetic or electrical polarization, vibrational properties, or any other applicable properties that may be used if it is desirable to enrich the EMDB 200 with electronic insulators, semiconductors, or conductors; materials having particular electronic, magnetic, mechanical, optical or other spectroscopic properties.

The preceding description is merely illustrative in nature and is in no way intended to limit the disclosure, its application, or uses. As used herein, the phrase at least one of A, B, and C should be construed to mean a logical (A or B or C), using a non-exclusive logical "or." It should be understood that the various steps within a method may be executed in different order without altering the principles of the present disclosure. Disclosure of ranges includes disclosure of all ranges and subdivided ranges within the entire range.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a compilation is not to the exclusion of other like items that may also be useful in the methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

What is claimed is:

1. An automated process for expanding an existing materials database (EMDB), the process comprising:
    providing a hypothetical materials database (HMDB), the HMDB comprising a compilation of hypothetical materials, each hypothetical material having:
        a hypothetical composition; and
        a crystal structure, including atomic coordinates in a unit cell and dimensions and shape of the unit cell; and
    performing a cyclical sub-process at least two times, the cyclical sub-process comprising:
        training a predictive model (PM) to generate a preliminary stability value for a material based on inputs of structure and composition, the training based on contents of the EMDB, the contents of the EMDB comprising a compilation of inorganic materials, and for each material in the compilation of inorganic materials:
            a composition;
            a crystal structure, including atomic coordinates in a unit cell and dimensions and shape of the unit cell; and
            a stability value;
        applying the PM to a set of hypothetical materials comprising at least a portion of the HMDB to produce a preliminary stability value for each hypothetical material in the set of hypothetical materials;
        selecting a subset of the set of hypothetical materials, the subset consisting of all hypothetical materials in the set having a preliminary stability value meeting a predetermined threshold value requirement;
        performing ab initio calculations on the subset, to determine a quantitative stability value for each hypothetical material in the subset, thereby converting each hypothetical material in the subset to a new material; and
        adding each new material in the subset, with its composition and crystal structure, to the EMDB to generate a larger EMDB with expanded contents that is used as a basis of training the PM in a next iteration of the cyclical sub-process,
    wherein iterative retraining of the PM based on the expanded contents of the larger EMDB iteratively improves accuracy and efficiency of the PM.

2. The process as recited in claim 1, further comprising: generating the HMDB by decorating one or more prototype crystal structures with selected chemical elements.

3. The process as recited in claim 2, wherein generating the HMDB comprises restricting the selected chemical elements to elements having electronegativity within a specified number of Pauling units of an average electronegativity of elements occupying the same site in known materials having the same prototype structure.

4. The process as recited in claim 2, wherein generating the HMDB comprises restricting the selected chemical elements to elements having atomic radius within a specified percentage of a radius of an element occupying the same site in known materials having the same prototype structure.

5. The process as recited in claim 1, wherein the set consists of a portion of the HMDB.

6. The process as recited in claim 1, further comprising creating the set of hypothetical materials by randomly selecting a portion of the HMDB.

7. The process as recited in claim 1, further comprising creating the set of hypothetical materials by selecting only hypothetical materials in the HMDB having an identical prototype crystal structure.

8. The process as recited in claim 1, further comprising creating the set of hypothetical materials by selecting only hypothetical materials in the HMDB having one or more of the same chemical elements.

9. The process as recited in claim 1, wherein the set is provided by selecting only hypothetical materials in the HMDB having all chemical elements in common.

10. The process as recited in claim 1, wherein the cyclical sub-process is performed for at least ten iterations.

11. The process as recited in claim 1, wherein the cyclical sub-process is performed for at least a hundred iterations.

12. The process as recited in claim 1, wherein the cyclical sub-process is repeated until the hypothetical materials available in the HMDB are exhausted.

13. The process as recited in claim 1, wherein the cyclical sub-process is repeated until the PM reaches a predictive accuracy identical to the ab initio calculations, as measured with respect to a ground-truth in the EMDB.

14. The process as recited in claim 1, wherein the cyclical sub-process further comprises removing each new material from the HMDB.

15. The process as recited in claim 1, wherein selecting the subset comprises creating a discard set including all hypothetical materials in the set not having a preliminary stability value meeting the predetermined threshold value requirement.

16. The process as recited in claim 15, further comprising deleting all hypothetical materials in the discard set from the HMDB.

17. An automated process for expanding an existing materials database (EMDB), the process comprising:
    performing a cyclical sub-process at least two times, the cyclical sub-process comprising:

training a predictive model (PM) to generate a preliminary stability value for a material based on inputs of structure and composition, the training based on contents of the EMDB, the contents of the EMDB comprising a compilation of inorganic materials, and for each material in the compilation of inorganic materials:
  a composition;
  a crystal structure, including atomic coordinates in a unit cell, and dimensions and shape of the unit cell; and
  a stability value;
applying the PM to a set of hypothetical materials comprising a portion of a hypothetical materials database (HMDB) to produce a preliminary stability value for each hypothetical material in the set of hypothetical materials, the HMDB a hypothetical materials database (HMDB), the HMDB comprising a compilation of hypothetical materials, each hypothetical material having:
  a hypothetical composition; and
  a crystal structure, including atomic coordinates in a unit cell; and
selecting a subset of the set of hypothetical materials, the subset consisting of all hypothetical materials in the set having a preliminary stability value meeting a predetermined threshold value requirement;
performing ab initio calculations on the subset, to determine a quantitative stability value for each hypothetical material in the subset, thereby converting each hypothetical material in the subset to a new material; and
adding each new material in the subset, with its composition and crystal structure, to the EMDB to generate a larger EMDB with expanded contents that is used as a basis of training the PM in a next iteration of the cyclical sub-process,
wherein iterative retraining of the PM based on the expanded contents of the larger EMDB iteratively improves accuracy and efficiency of the PM.

18. The process as recited in claim 17, further comprising generating the HMDB prior to performing the cyclical sub-process.

19. The process as recited in claim 17, further comprising:
creating the set of hypothetical materials; and
removing from the HMDB all hypothetical materials in the set of hypothetical materials.

20. The process as recited in claim 19, wherein creating the set comprises randomly selecting a portion of the HMDB.

* * * * *